United States Patent
Killgore et al.

(10) Patent No.: US 11,058,778 B2
(45) Date of Patent: Jul. 13, 2021

(54) NANOPARTICLE PHARMACEUTICAL DELIVERY SYSTEM

(71) Applicant: ADEIRA PHARMA, LLC, St. Louis, MO (US)

(72) Inventors: Kendall Killgore, St. Louis, MO (US); John Hefti, St. Louis, MO (US)

(73) Assignee: ADEIRA PHARMA, LLC, St. Louis, MO (US)

( * ) Notice: Subject to any disclaimer, the term of this patent is extended or adjusted under 35 U.S.C. 154(b) by 44 days.

(21) Appl. No.: 16/575,718

(22) Filed: Sep. 19, 2019

(65) Prior Publication Data
US 2021/0085802 A1    Mar. 25, 2021

(51) Int. Cl.
| | |
|---|---|
| A61K 47/69 | (2017.01) |
| A61K 9/51 | (2006.01) |
| A61K 31/225 | (2006.01) |
| A61K 47/14 | (2017.01) |
| A61K 47/68 | (2017.01) |
| A61K 47/44 | (2017.01) |
| A61K 31/337 | (2006.01) |

(52) U.S. Cl.
CPC ........ *A61K 47/6929* (2017.08); *A61K 9/5192* (2013.01); *A61K 31/225* (2013.01); *A61K 31/337* (2013.01); *A61K 47/14* (2013.01); *A61K 47/44* (2013.01); *A61K 47/6803* (2017.08); *A61K 47/6855* (2017.08)

(58) Field of Classification Search
CPC .. A61K 47/6929; A61K 9/5192; A61K 47/44; A61K 47/6855; A61K 47/14; A61K 31/337; A61K 31/225; A61K 47/6803
See application file for complete search history.

(56) References Cited

U.S. PATENT DOCUMENTS

| | | | |
|---|---|---|---|
| 10,245,234 | B1 | 4/2019 | Lele |
| 10,251,837 | B2 | 4/2019 | Huang |
| 10,342,846 | B2 | 7/2019 | Bilgicer et al. |
| 2019/0231815 | A1 | 8/2019 | Voelkel |
| 2019/0240164 | A1 | 8/2019 | Shoyele |

FOREIGN PATENT DOCUMENTS

| | | |
|---|---|---|
| WO | 2019/133914 A1 | 7/2019 |
| WO | 2019/168921 A1 | 9/2019 |

OTHER PUBLICATIONS

International Search Report and Written Opinion for PCT/US2020/050732 dated Dec. 15, 2020, 9 pages.
Lanza et al., "Targeted Antiproliferative Drug Delivery to Vascular Smooth Muscle Cells With a Magnetic Resonance Imaging Nanoparticle Contrast Agent," Circulation, 2002, pp. 2842-2487, vol. 106, No. 22.
Pham et al., "Variable Antibody-dependent Activation of Complement by Functionalized Phospholipid Nanoparticle Surfaces," J. Biol. Chem., 2011, pp. 123-130, vol. 286.

*Primary Examiner* — Robert S Cabral
(74) *Attorney, Agent, or Firm* — Polsinelli PC

(57) ABSTRACT

A method of preparing a nanoparticle pharmaceutical delivery system. A nanoparticle pharmaceutical delivery system. A method of preparing a targeted nanoparticle pharmaceutical delivery system. A targeted nanoparticle pharmaceutical delivery system.

5 Claims, 4 Drawing Sheets

NANOPARTICLE PHARMACEUTICAL DELIVERY SYSTEM

FIELD OF THE INVENTION

A nanoparticle pharmaceutical delivery system is disclosed.

BACKGROUND

Many small molecule therapeutics, such as taxanes like paclitaxel and docetaxil, and the platinum derivatives like cisplatin and carboplatin, are highly effective medical therapeutics. However, many small molecules are difficult to formulate for parenteral administration because of their low aqueous solubilities and/or high toxicities. For example, the first commercially available formulation of paclitaxel used Cremophor EL as a cosolvent, which has been shown to cause serious side effects such as hypersensitivity, neurotoxicity, and neuropathy. Subsequently, a protein-bound PTX formulation (Abraxane) was developed and approved by the FDA in 2005 and is now widely adopted, though the improvement in efficacy over PTX in Cremophor EL is modest. There exist large libraries of small chemical entities that may, or are known to, have important therapeutic benefits, but suffer from the inability to be effectively and safely formulated. There is a compelling need for new or alternative formulations of small molecule therapeutics and potential therapeutics that provide stable formulations, reduced toxicity, and improved efficacy, optionally by targeting the therapeutic to specific cells and tissues within the body that are involved with disease pathophysiology.

SUMMARY

Disclosed is a nanoparticle formulation for delivery of small molecule therapeutics in a stable, and optionally targeted, delivery platform that s able to deliver one or more active pharmaceutical ingredients (API) contained in lipid-based nanoparticles that range in size from 30 to 225 nanometers in diameter.

More particularly, Applicants' disclosure provides for a stable, pharmaceutically acceptable, nanoparticle solution comprising: 12-28% (v/v) type 1 safflower oil; 1.5-12% (v/v) triacetin; 1.5-5.0% (w/v) surfactant commixture of dipalmitoylphosphatidylcholine and dipalmitoylphosphatidylglycerol; 0.1 to 0.6% (w/v) therapeutically active small molecule therapeutic, optionally a taxane or a platinum derivate; and 1-4% (w/v) glycerin in buffered water at pH below 8.0.

The solutions comprising Applicants' disclosure are preferably buffered at a pH of between 4.0 and 7.5. Preferred buffers include tartrate, phosphate, Tris, citrate, or calcium ethylenediaminetetraacetic acid (EDTA). The solutions of this invention preferably contain nanoparticles where 95% of the nanoparticles are between 30 and 200 nm in diameter. It is also preferred that the solutions of this invention contain at least one small molecule chosen for therapeutic benefit, in concentration between 0.1 and 10.0 mg/ml.

The surfactant commixture or the fully formulated nanoparticle may optionally contain a targeting agent directed to a structure on a target cell. Targeting agents include monoclonal antibodies (mAb), antibody fragments and peptidomimetics, the latter consisting of molecular entities that possess affinity to specific biological targets of medical interest, but are not necessarily proteins. Therapeutic antibodies may also be incorporated onto the nanoparticles, either monovalent, bispecific or polyvalent. The invention is exemplified with a therapeutic monoclonal antibody that targets the HER2 receptor on tumor cells, which is a well-known target for cancer therapeutics.

Applicants' disclosure further provides for a method for encapsulating a therapeutically effective amount of a small molecule therapeutic to reduce toxicity and/or improve efficacy in a patient wherein the method comprises: encapsulating the API in a nanoparticle where the nanoparticles are in an agurous solution, the nanoparticle solution comprising: 12-28% (v/v) type 1 safflow oil; 1.5-12% (v/v) triacetin; 1.5-5.0% (w/v) surfactant commixture of dipalmitoylphosphatidylchohne and dipalmitoylphosphatidylglycerol; 0.1 to 0.6% (w/v) therapeutically active API, 1-4% (w/v) glycerin in buffered water at pH below 8.0. The preferred APIs, buffers, nanoparticle sizes and concentration of taxanes are as described above for the solutions. The components of the surfactant commixture and targeting agents are also as provided above for the solutions of this invention.

Applicants' disclosure also provides for a method of delivering a therapeutically effective amount of an API to a patient in need thereof, where the method comprises the step of administering the therapeutically effective amount of API in a stable, pharmaceutically acceptable and well-tolerated nanoparticle solution, the solution comprising: 12-28% (v/v) type 1 safflower oil, 1.5-12% (v/v) triacetin, 1.5-5.0% surfactant commixture of dipalitoylphosphatidylcholine and dipalmitoylphosphatidylglycerol; 0.1 to 0.6% (w/v) therapeutically active API, 1-4% (w/v) glycerinin buffered water at pH below 8.0. The preferred APIs, buffers, nanoparticle sizes and concentration of API are as described above for the solutions. The components of the surfactant commixture and targeting agents are also as provided above for the solutions of Applicants' invention.

DETAILED DESCRIPTION OF THE PREFERRED EMBODIMENTS

Figure 1:
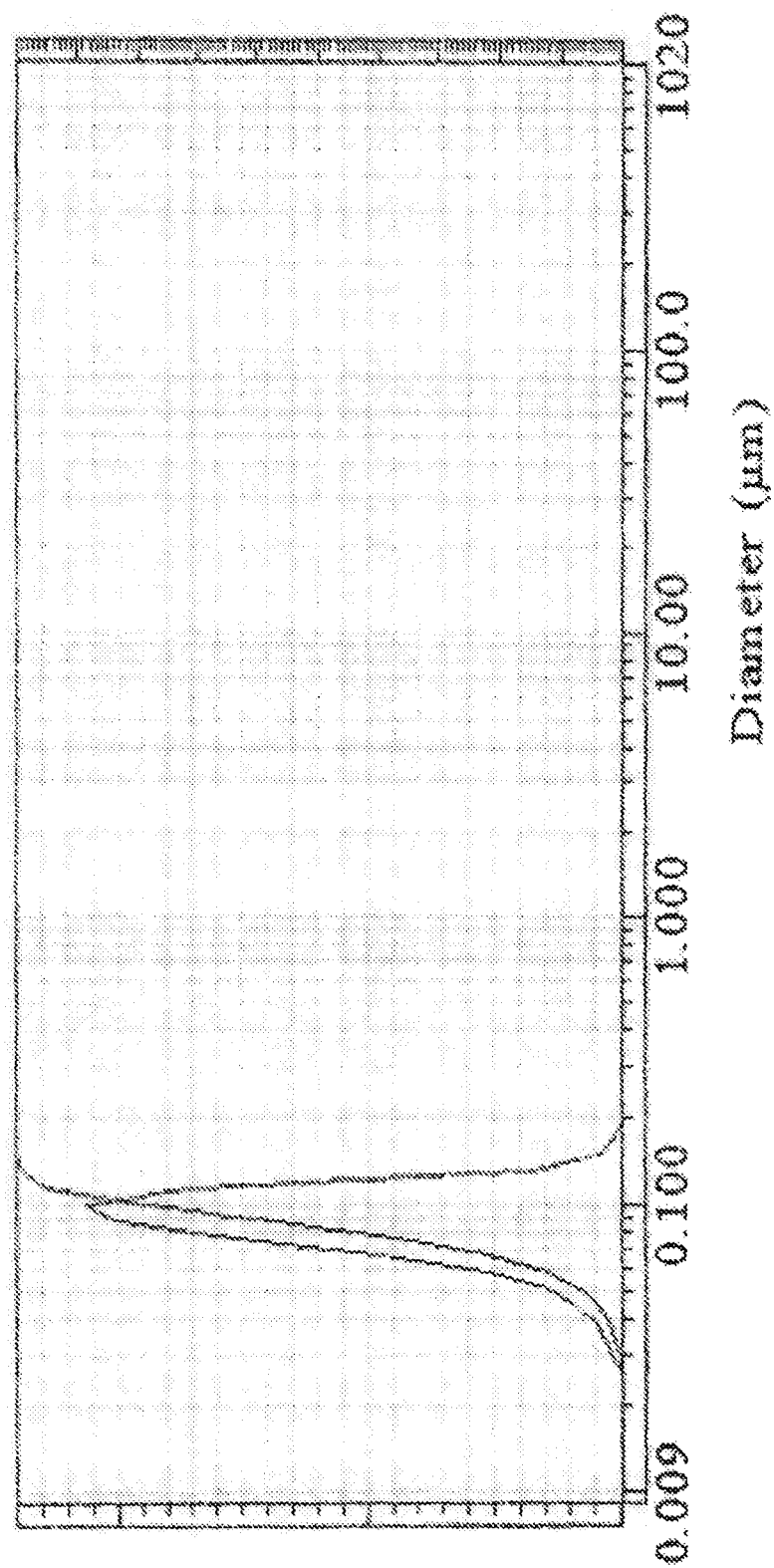
FIG. 1 graphically recites a histogram showing particle number as a function of size.

Applicants' nanoparticle pharmaceutical delivery system is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicants' disclosure may be combined in any suitable manner in one or more embodiments. In the following description, numerous specific details are recited to provide a thorough understanding of embodiments of the invention. One skilled in the relevant art will recognize, however, that Applicants' disclosure may be practiced without one or more of the specific details, or with other methods, components, materials, and so forth. In other instances, well-known structures, materials, or operations are not shown or described in detail to avoid obscuring aspects of Applicants' disclosure, and it will be appreciated by those skilled in the art that it is intended to cover alternatives, modifications, and equivalents as may be included within the spirit and scope of Applicants' disclosure as defined by the appended claims and their equivalents as supported by the following disclosure and drawings.

In certain embodiments, Applicants disclose a method to form a Nanoparticle Pharmaceutical Delivery System and a Nanoparticle Pharmaceutical Delivery System formed by Applicants' method. In certain of these embodiments, both the method, and the composition formed by the method, utilize/comprise one Active Pharmaceutical Ingredient ("API"). In other of these embodiments, both the method, and the composition formed by the method, utilize/comprise more then one Active Pharmaceutical Ingredient ("API").

In certain embodiments, Applicants disclose a method to form a Targeted Nanoparticle Pharmaceutical Delivery System and a Targeted Nanoparticle Pharmaceutical Delivery System formed by Applicants' method. In certain of these targeted embodiments, both the method, and the composition formed by the method, utilize/comprise one Active Pharmaceutical Ingredient ("API"). In other of these targeted embodiments, both the method, and the composition formed by the method, utilize/comprise more then one Active Pharmaceutical Ingredient ("API").

A. Introduction

Many small molecules, such as taxanes and platinum derivatives, are widely used chemotherapeutic agents for the treatment of cancer, owing to their potency as anti-tumor agents for many different cancer types. However, despite their widespread use they suffer from several limitations that reduce their efficacy and safety. First, many small molecules, such as the taxanes, and especially paclitaxel, have very poor solubility in aqueous media such as buffers and blood plasma. Current methods to solubilize such APIs include cosolvents, which may be toxic and cause hypersensitivity reactions in many patients.

More broadly, there exist many small molecules that are demonstrated to have desired activities on models of human diseases, but suffer from a ready means to be formulated for safe administration in patients. In some cases, lack of aqueous solubility prevents the small molecule from being safely delivered to patients, sometimes requiring toxic excipients to aid solubility. In other cases, potential small molecule therapeutics cannot be delivered to the appropriate sites of action within a patient, and thus are rendered less effective. Biodistribution of therapeutic formulations is a frequent challenge in the therapeutic setting, especially for lipophilic small molecules that partition into lipid-rich volumes of the human body and are thus unavailable therapeutically. For these reasons it is desirable to have a formulation system that is capable of containing therapeutic small molecules such that they are distributed to areas or volumes within the body involved in the disease.

Many currently approved formulations are not targeted, relying instead on passive biodistribution to reach the site of intended activity in adequate amounts to be clinically effective. Newer attempts at nanoparticle formulations, some of which are targeted, suffer from an inability to load clinically significant or optimal amounts of API onto the nanoparticles, rendering them inadequate as therapeutics. Currently available targeted therapeutics do not include a therapeutic antibody, either as a single therapeutic entity or in combination with other pharmacologically active molecules.

From a pharmacologic perspective, both nanoparticle size and stability are important. Since therapeutics are formulated remotely and stored for indefinite periods of time before administration, it is important that any nanoparticle formulation remain stable for the duration of time between formulation and use to insure that the therapeutic is given as specified. Breakdown of nanoparticles resulting in non-homogeneous mixtures not only lose efficacy, but can actually be dangerous. For example, large pools of lipids can cause transient hypoxia in vital tissues such as those found in the nervous system and in cardiac muscle. This can cause serious side effects such as embolic stroke and myocardial infarction.

The size of the nanoparticles is important for at least two reasons. First, parenterally administered nanoparticle formulations are initially introduced into the body through the vasculature. However, many disease targets occupy volumes outside any blood vessels. Thus it is important for intravascular therapeutics to be small enough to extravasate through junctions in the vasculature to reach the site of intended activity. Although this process is helped, for example, by the inherent leakiness of the angiogenic vessels that surround tumors, larger particles (for example, greater than 200 nanometers in average diameter) have commensurately less tendency to pass from the plasma to the interstitial space around the tumor, and thus commensurately lower efficacy. In addition, larger average diameter nanoparticles are generally less stable and may decompose in plasma, which may cause similar problems to inhomogeneous lipid mixtures described above.

In the disclosure herein, methods and compositions of stable and appropriately sized API-containing nanoparticle formulations are presented that allow distribution of therapeutically efficacious amounts of API. Applicants' formulation comprises one or more lipids, at least one of which is chosen for its ability to dissolve the API and another of which is chosen for its ability to form stable lipid nanoparticles when combined with certain surfactants. In many cases, both lipids are the same. The addition of an optional lipid-anchored targeting ligand with high affinity to surface proteins selectively expressed on many cancer cells and the surrounding tumor vasculature, or other disease targets, provides a means to target the API-containing nanoparticles to cells and tissues directly involved with many cancers, as well as provide therapeutic benefit, for example, though the use of a therapeutic mAb as the targeting ligand.

B. Definitions

Lipid: As used herein, a lipid refers to a non-polar hydrophobic molecule or a plurality of molecules characterized by longer chain hydrocarbons. Lipids may be comprised of mixtures of one or more fatty acids like oleic, linoleic, stearic and/or palmitic acids. For example, safflower oil is a naturally produced mixture of fatty acids and small amounts of other components, which is commonly used for parenteral nutrition and other medical uses. Another example is triacetin, the tri-ester of glycerol and acetic acid, which dissolves small lipophilic molecules such as the taxanes, and is also routinely used for parenteral nutrition.

Surfactant: As used herein, a surfactant is an amphipathic molecule that includes a polar, hydrophilic domain, and a non-polar, hydrophobic domain. Examples include the large class of amphipathic compounds known as phosopholipids, which have a phosphate group that comprises the polar domain, and one or more long chain fatty acids that comprise the non-polar domain.

Nanoparticle: As used herein, a nanoparticle refers to a surfactant-stabilized lipid-based particle with a mean and median particle diameter between 60 nanometers and 225 nanometers when residing in an aqueous buffer or media.

Emulsion: As used herein, an emulsion refers to a combination of lipids and surfactants in an aqueous buffer or media. Specific subtypes of emulsions include crude emulsions, in which the aqueous and lipid phases are inhomogeneously and/or incompletely mixed; and fine emulsions, in which most or all of the lipid components are contained in surfactant-stabilized nanoparticles that are homogeneously distributed in an aqueous buffer.

Active Pharmaceutical Ingredient (API): As used herein, an API is one or more molecular entities that have desired pharmacologic and therapeutic activities. An API may be comprised of a small molecule of synthetic or natural origin, a protein or fragment thereof, therapeutic antibodies and fragments thereof, or other biologic or chemical entity that is known to, or suspected of, having pharmacologic activity. Examples of APIs include paclitaxel, docetaxel, other taxane derivatives, and cisplatin and other platinum derivatives.

Targeting ligand: As used herein, a targeting ligand is a molecular structure that is attached to the outermost volume of the nanoparticle, optionally in the surfactant layer that stabilizes the nanoparticles, and has binding affinity to a specific class of in vivo biologic structures or targets of therapeutic interest. The targeting ligand may be a small molecule, a peptidomimetic, an antibody or antibody fragment, optionally chosen for pharmacologic activity, a protein, or other molecular entity.

Target: As used herein, a target refers to a naturally occurring in vivo structure that possesses affinity to the targeting ligand. A target may include proteins that are expressed on the surfaces of certain biological cells, such as cancer cells and endothelial cells in the vasculature surrounding a tumor. An example of a target is the HER2 receptor, a protein that is selectively expressed on the surface of certain cancer cells.

C. Stable Pharmaceutically Acceptable Nanoparticle Solutions

The materials used in the invention are comprised of lipids, surfactants, buffers and active pharmaceutical ingredients (APIs), as defined above. In general, the choice of lipids depends on the API being used, as different APIs may require different lipids to be dissolved. In the case of the taxanes, triacetin is an example of a lipid that works well to dissolve the API. The other factor affecting choice of lipid is nanoparticle stability. As described in detail in example 6, many lipids do not form stable nanoparticles; and of those that do, many do not dissolve the API. In addition, certain lipids that form stable nanoparticles alone will not do so if they are mixed with a solubilizing lipid such as triacetin. Thus, in accordance with the invention described herein, the following materials are presented in order to more carefully describe the methods and composition of this class of nanoparticle formulations.

Materials

Type 1 safflower oil: Type 1 safflower oil is a naturally produced plant-based lipid that contains a predominance of linoleic acid, typically in the range of 70-85% of the total lipid content of safflower oil. Other major lipids include oleic acid, stearic acid, and palmitic acid. Other minor constituents may also be present in safflower oil. USP-grade safflower oil may be purchased by vendors such as Croda, Inc.

Triacetin: This nine-carbon lipid is the tri-ester of glycerol and acetic acid, and is the principal lipid responsible for dissolving the taxanes. USP-grade triacetin can be purchased from a number of vendors, including Sigma-Aldrich, Inc., and Spectrum Chemical, Inc.

Surfactant commixture: The surfactant commixture is comprised of a mixture of surfactants. The individual components of the commixture may include lecithin (Lipoid GmbH, Ludwigshaven, Del.), and 1,2-dipalmitoyl-sn-glycero-3-phosphoglycerol (DPPG, Lipoid GmbH, Ludwigshaven, Del.). The surfactant commixture may optionally contain a targeting ligand, such as the $\alpha_v\beta_3$-targeting peptidomimetic described below, or it may contain a surfactant that binds an appropriately prepared targeting ligand, such as DSPE-PEG-biotin, which binds a mAb that has streptavidin conjugated to the Fc portion of the antibody.

Taxane derivatives: Taxanes may optionally be used as the API. Taxanes are diterpines that are produced by plants of the genus Taxus. They are a class of small molecules that are widely used in cancer chemotherapy and other medical uses. Taxanes include, but are not limited to, compounds that are structurally similar to or are in the same general chemical class such as paclitaxel (i.e., taxol), docetaxel (i.e., taxotere), or ortataxel, and pharmaceutically acceptable salts, derivatives, or analogs of paclitaxel, docetaxel, and ortataxel.

Their mechanism of action is to stabilize microtubules in dividing cells, effectively preventing cell division by blocking disassembly of the microtubules. Paclitaxel was the first taxane to be purified and used as a chemotherapeutic agent, and is still widely used. Docetaxel is a more recent taxane, which has also found widespread use as a cancer chemotherapeutic agent. In 2010 Cabazitaxel, another taxane derivative, was approved for use in certain cancers. Purified USP-grade paclitaxel and docetaxel may be purchased from a number of vendors, including Tecoland, Inc.

Buffers: The aqueous phase of the formulation is comprised of a buffer such as tartrate. These buffers may be purchased pre-mixed (Sigma-Aldrich) or formulated from purified water (Calbiochem) and the individual constituents, including tartaric acid (J.T. Baker), sodium phosphate monobasic monohydrate (Mallinckrodt), glycerin (Mallinckrodt), hydrochloric acid (VWR), and sodium hydroxide (VWR).

Targeting ligand: As defined previously, a targeting ligand is a molecular structure that has binding affinity to a specific class of in vivo biologic structures of therapeutic interest. One such targeting ligand used in the invention described herein is a monoclonal antibody (mAb) that is chosen for its specificity to a desired target. For example, a mAb specific for HER2, where specificity is defined as having at least four-fold greater affinity for HER2 than for related or unrelated protein targets, is used to target the nanoparticle to the HER2 receptor that is highly expressed on certain cancer cells. Other examples include peptidomimetics, fragments of monoclonal antibodies, and other proteins and small molecules that have specific affinities for biological targets. The targeting ligand may be incorporated into the nanoparticle during the formulation of the fine emulsion, for example by including a peptidomimetic conjugated to a surfactant, or the targeting ligand may be incorporated into the nanoparticle post-formulation, for example by incorporating at least one streptavidin molecule onto the Fc portion of the mAb and including a biotinylated surfactant in the formulation.

Process for Making

Formulation begins by dissolving the API, for example a taxane, in a lipid that dissolves the API, for example triacetin in the case of a taxane, using heat and sonication. A crude mixture of the API in the solvent or suspending lipid at concentrations below the molar solubility of the API in the lipid is heated by a water-bath and the API is dissolved or suspended using sonication. This process continues until the API precipitate is entirely dissolved in the solvent lipid, as evidenced by the lack of any precipitate in the mixing vessel and a clear appearance of lipid.

Next, the individual components of the surfactant commixture are suspended in an appropriate buffer containing glycerin with high-shear dispersion, using any of the readily available high-shear laboratory mixers (for example an Ultra-Turrax high shear mixer available from Homogenizers, Inc.). This is followed by addition of the safflower oil and the API/lipid solution, followed by additional high-shear mixing.

This crude emulsion is then processed into a fine emulsion using a high-pressure microfluidizer such as a M110Y or M110EH Microfluidics emulsifier (Microfluidics, Newton, MA) at approximately 10,000-25,000 pounds per square inch for a predefined number of passes through the fluidic circuit, until a fine emulsion of nanoparticles has been achieved. The number of passes is determined by first measuring the flow rate. The volume of the crude emulsion is then multiplied by the desired number of passes and then finally divided by the previously determined flow rate to yield a time duration of processing that will result in the desired number of passes. If a fine emulsion is not achieved with an initial phase of processing, the number of passes may be extended to achieve the desired formulation, optionally by monitoring the particle size in real time and adjusting and/or curtailing the process after the desired particle size is achieved.

During the microfluidization (emulsification) process the emulsion is kept cool by routing part of the fluidic circuit through a cooling bath. For example, a VWR Model 1175MD refrigerated circulator filled with 1:1 glycol/water can be connected to the Process Fluid Heat Exchanger of the M-110EH Microfluidizer to maintain the temperature of the emulsion near 5° C. The combination of high pressure and high shear fluid flow tends to heat up the emulsion, which can limit the formation of nanoparticles and/or degrade existing nanoparticles.

Once the emulsion is formed it is initially characterized according to particle size using dynamic or static light scattering methods on a calibrated analytic system intended for such uses (for example a Horiba LA-910 static light scattering particle size distribution analyzer). Typical desired particle sizes span the mean and median range from 60 nanometers to 225 nanometers, without appreciable evidence of any particle populations greater than 1 micrometer. Additional characterization includes visual inspection for homogeneity, formation of precipitates and pooling of lipids. The concentration of the API in the processed fine emulsion is measured using high-performance liquid chromatography (HPLC) or inductively coupled plasma mass spectrometry (ICP-MS). A standard curve is run on the HPLC, followed by test samples of the fine emulsion to determine the amount of API present.

Once the fine emulsion is formulated, a targeting ligand is optionally attached to the outermost portion of the nanoparticles using the appropriate binding chemistries. Such chemistries include the 'click' chemistries, as is well known in the art, or it may utilize the very strong biotin-streptavidin reaction commonly used in many areas of biology and chemistry. The latter example has the benefit of simplicity and the lack of additional reagents or reaction conditions to achieve binding.

Once the processed emulsion passes the initial characterization criteria, as outlined previously, it is placed into appropriately sized containers and sterilized. The sterilization method is optionally chosen to be either heat and pressure sterilization using available equipment designed for this purpose; or using the process of sterile filtration using 32 mm Pall Acrodisc PF syringe filters with 0.2 μm Supor membranes, in which the emulsion is passed through a size-based filter that is chosen such that the nanoparticles pass freely but microorganisms do not. The latter method may be preferable in cases where a protein or antibody fragment is used for the targeting ligand. Optionally, the formulation is sterilized before conjugating the targeting ligand.

Additional follow-up characterization of particle size and amount of API present is done after sterilization to insure nanoparticle integrity, emulsion stability, and to quantitate the amount of API. Relatively small increases in mean and median diameters in the first week after formulation are acceptable (<20%), but continued increases in diameter beyond the first week, or the appearance of particles greater than 1 micrometer in diameter at any time, indicate instability in the formulation.

Presence and quantity of the API are measured using any of the well-known methods for bioanalysis, such as mass spectrometry or HPLC. In the case of HPLC, reference standards for calibration are prepared and used to quantitate the results of the HPLC analysis on the formulation. HPLC analysis measures the amount of API as a percentage of an ideal recovery. For example, if 2.0 mg/ml of paclitaxel is theoretically incorporated into a nanoparticle formulation, an acceptable recovery might be 1.8 mg/ml, for a 90% recovery. Recoveries of the API are used to determine dosing levels for subsequent studies in which the analyzed formulation is used. In addition, low recoveries (<60%) may indicate a formulation problem. It is also useful to periodically analyze archival amounts as representative of a batch of formulation that is used in in vivo or in vitro studies, to determine the actual amounts of API being used in the studies and to determine if the API is coming off the nanoparticles.

If the nanoparticles are optionally targeted, it is possible to verify that the nanoparticles have the desired affinity to their intended target using the appropriate method. For example, a fluorescent dye such as rhodamine may be incorporated into the nanoparticle, and the resulting nanoparticles are then exposed to cells that express the intended target, for example in a flow cytometer. A comparison may then be made between targeted and untargeted nanoparticles, and between cells that express the target and cells that do not. A pre-defined difference in fluorescence, for example a three-fold difference, is used to determine suitable affinity for the nanoparticles to the intended target.

Finally, formulations are also characterized by visual inspection to insure homogeneity, lack of precipitates and pooling or separation of lipids from the aqueous buffer.

Once the individual containers are sealed and sterilized, they are stored at approximately ±5° C., but not frozen.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those skilled in the art will readily recognize a variety of noncritical parameters that could be changed or modified to yield essentially similar results.

Example 1—Formulation of a HER2-Targeted Paclitaxel-Containing Nanoparticle Emulsion In the following example we provide the steps for preparing a HER2-targeted nanoparticle emulsion of paclitaxel.

The reagents used for this exemplary formulation, along with the sources for these materials, are listed in table 1 below.

TABLE 1

| Reagent | Manufacturer |
| --- | --- |
| Water for Injection (WFI) | Calbiochem |
| Tartaric Acid, Granular | J. T. Baker |
| Sodium Phosphate Monobasic Monohydrate | Mallinckrodt |
| Glycerin | Mallinckrodt |
| 1N Hydrochloric Acid (HCl) | VWR |
| 1N Sodium Hydroxide (NaOH) | VWR |
| EPCS Egg Lecithin | Lipoid |
| Dipalmitoylphosphatidylglycerol (DPPG) | NOF |
| mPEG-DSPE, MW 1000 | Nano-soft Polymers |
| DSPE-PEG-biotin, MW = 2000 | Nanocs |
| Targeting Ligand (HER2 mAb conjugated to streptavidin) | BioLegend |
| Safflower oil | Spectrum |
| Triacetin | Spectrum |
| Paclitaxel | Tecoland |

To prepare the nanoparticle solution in this example, the following equipment was used:

Ultra-Turrax high-shear mixer.

Microfluidics M-110Y Microfluidizer to process crude emulsion to give fine emulsion.

Sterile filtration using a Pall Acrodisc PF filters w/0.2 µm Supor membranes.

Horiba LA-910 static light scattering particle size distribution analyzer for particle size determination.

A tartrate buffer was first prepared by dissolving 1.13 grams of tartaric acid in 1 liter water for injection (WFI) with stirring via magnetic stirrer. Next, 22 grams of glycerin were transferred to the solution using a pipette, then stirred. The pH of the buffer was brought to 7.0 with 1 N NaOH, as measured using Orion 720 A+pH meter equipped with a ROSS Ultra pH electrode, and placed in a 1 liter volumetric flask. The final volume was brought to 1 liter using WFI.

Next, the 250 mg of paclitaxel was solubilized in 5 ml of triacetin by water-bath sonication at 50° C., using 50 milligrams of paclitaxel per one milliliter of triacetin. The paclitaxel was heated and sonicated until there was no more visible precipitate and the solution was transparent.

Next, the surfactant commixture was prepared. The components of the surfactant commixture included 1.40 g Lipoid EPCS egg phosphatidylcholine (Lipoid GmbH, Ludwigshaven, Del.), 0.60 g of 1,2-dipalmitoyl-sn-glycero-3-phosphoglycerol (DPPG, NOF Corporation, Tokyo, JP), 150 mg of DSPE-PEG-biotin MW 2000 (DSPE-PEG2K-biotin, Nanocs Inc., New York, N.Y.) and 5 mg of mPEG-DSPE MW 1000 (DSPE-PEG1K, Nanosoft Polymers, Winston-Salem, N.C.). These components were pre-mixed in 32 mL of pH 7.0 tartrate buffer with 22 mg/mL glycerin in a 100 mL disposable beaker using the Ultra-Turrax high shear mixer for 30 seconds. This was followed by addition of 13 ml of Type 1 safflower oil and the paclitaxel/triacetin solution prepared above, followed by an additional 2 minutes of mixing on the high shear mixer to give the crude emulsion.

This crude emulsion was then further emulsified on a M110Y Microfluidics emulsifier (Microfluidics, Newton, Mass.) at approximately 15,000 pounds per square inch for 50 passes, using the method described previously. The temperature of processing was maintained at approximately 5° C. by using an ice bath to cool the Process Fluid Heat Exchanger of the Microfluidizer.

The emulsion was buffered to a pH of 7.0, and characterized by particle size and distribution via static light scattering (FIG. 1). The mean particle size was found to be 80 nm, without evidence of particles larger than 200 nm. There were no visible signs of lipid pooling or phase separation, and the fine emulsion appeared homogeneous. The process above resulted in approximately 50 ml of fine nanoparticle emulsion.

The 50 ml volume of the fine emulsion was sterile filtered using Pall Acrodisc PF filters w/0.2 µm Supor membranes, followed by a particle size measurement and HPLC analysis. It was then placed into multiple Wheaton serum sample vials, each with 5 mL of emulsion and ~4 mL headspace, followed by nitrogen sweep, capping and sealing (gray butyl rubber caps with Flip-Off seals, obtained from West Pharmaceuticals). The mean particle size had not changed after sterile filtration, and HPLC analysis confirmed a recovery of 89% of the paclitaxel.

Samples were stored at 2-8° C., not frozen, and characterized weekly thereafter via static light scattering and HPLC. Mean particle diameter did not increase with time, and subsequent HPLC analyses showed consistent recoveries in the range of 90%.

A targeting ligand in the form of an anti-HER2 mAb, a therapeutic antibody, was conjugated to the above nanoparticle formulation as follows: A vial containing a 4 mg/ml concentration of anti-HER2 mAb with at least one streptavidin (SAV) molecule covalently connected to the Fc portion of the majority of antibodies was purchased from BioLegend, Inc. This vial, along with the biotinylated emulsion and all the necessary equipment, as described below, was wiped into a Class 5 hood at room temperature using 70% EtOH. Using a cross-shaped magnetic stirring bar that had been wiped into the hood, the biotinylated emulsion was stirred at medium speed on a magnetic stir plate that had been wiped into the hood. Using a transfer pipette that has been wiped into the hood, an amount of the SAV-mAb conjugate was transferred to a sterile 10 mL burette with a PTFE stopcock, the amount chosen was such that the final concentration when added to the emulsion would be 0.295 mg/ml. The filled burette was then clamped in place above the vial containing the biotinylated emulsion that was being stirred. The SAV-mAb conjugate in the burette was then added drop-wise into the biotinylated emulsion, until the burette was empty. The emulsion was then stirred for an additional ten minutes. Stirring was then discontinued, and the magnetic bar was removed using a magnet that had been wiped into the hood. The vial was swept with purified nitrogen and sealed with pre-sterilized stopper (West Pharma). The vial was then removed from the Class 5 hood and sealed with an appropriately sized Flip-Off seal. The vial was then placed on a carousel inverter at room temperature and continuously inverted at low speed for two hours. The vial was then stored between 2-8° C.

Example 2. Characterization of Nanoparticle Formulation

A paclitaxel nanoparticle emulsion was prepared substantially as described in example 1, with 5.0 milligrams of paclitaxel per milliliter of fine nanoparticle emulsion, then terminally sterilized using heat and pressure and stored at +5° C. for one week. The distribution of particle sizes, including mean and median particle sizes, were determined using a static light scattering particle size analyzer (Horiba Instruments, Inc., Irvine, Calif.). The particle sizes showed a mean and median diameter of approximately 80 nanometers (FIG. 1). The distribution of particle sizes was narrowly and symmetrically distributed around the mean and median diameter, with no populations of particles larger than 250 nm, indicating a stable fine emulsion of nanoparticles.

Presence and quantity of the API was measured using high-performance liquid chromatography (HPLC), as described previously. The recovery after one week was 86.2%, indicating adequate API on the nanoparticles and good stability.

Finally, the nanoparticle formulation was characterized by visual inspection, and noted to be homogeneous, without precipitates or visible phase separation.

Example 3: In Vivo Efficacy and Toxicity of an Exemplary Targeted Paclitaxel-Containing Nanoparticle Emulsion To demonstrate the therapeutic potential of the invention described herein, the following studies were carried out in mouse xenograft models of cancer.

Animal Models: Female athymic nude mice (Crl:NU (Ncr)-Foxn1nu, Charles River) that were eight weeks old and had a body weight (BW) range of 19.0-24.8 grams (g) on Day 1 of the study were used. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-o'cobs™ Laboratory Animal Bedding in static microisolators on a 12-hour light cycle at 20-22° C. (68-72° F.) and 40-60% humidity.

Tumor Cell Culture: MDA-MB-231 breast cancer cells were grown to mid-log phase in RPMI 1640 medium containing 10% fetal bovine serum, 2 mM glutamine, 100 units/mL sodium penicillin G, 25 μg/mL gentamicin, and 100 μg/mL streptomycin sulfate. The tumor cells were cultured in tissue culture flasks in a humidified incubator at 37° C., in an atmosphere of 5% CO2 and 95% air.

Tumor Implantation and Measurement: The MDA-MB-231 cells were harvested during exponential growth and resuspended cold in PBS. Each test animal received a subcutaneous (s.c.) injection of 5×10$^6$ MDA-MB-231 cells (0.1 mL cell suspension) into the right flank, and tumor growth was monitored as the average tumor size approached the target range of 100-150 mm$^3$. Tumors were measured in two dimensions using caliper measurement of length and width.

Eighteen days after tumor cell implantation, on Day 1 of the study, mice bearing appropriately sized tumors were sorted into six groups of ten mice each (n=10). The individual tumor volumes range from 75 to 144 mm$^3$ and the group mean tumor volumes were 106-108 mm$^3$.

Figure 2:
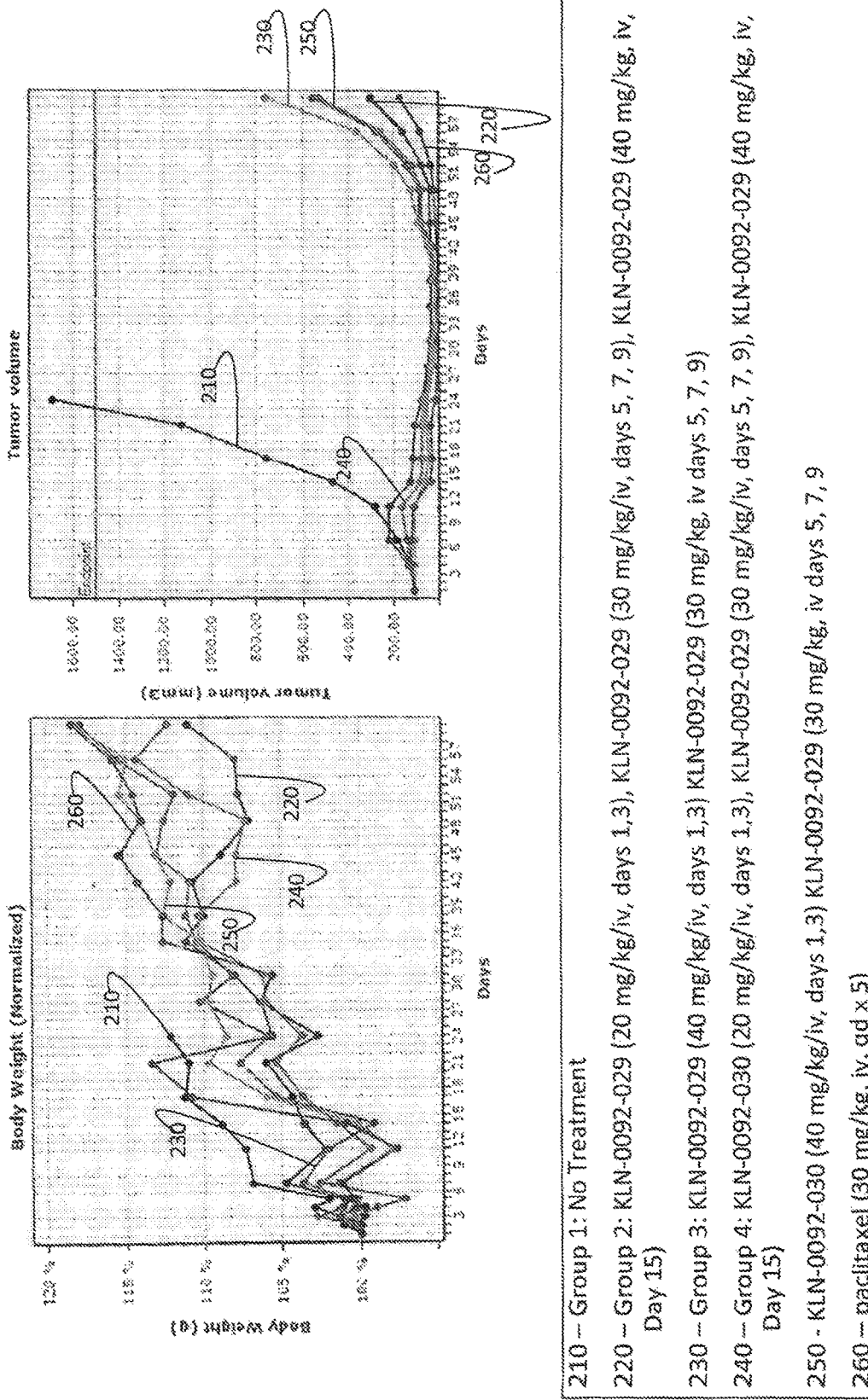
FIG. 2 graphically recites body weight changes, and tumor volume changes, over time for each treatment group identified.

Referring now to FIG. 2, two $\alpha_v\beta_3$-targeted paclitaxel-containing nanoparticle emulsions were prepared and fully characterized. Targeting was achieved by inclusion of a peptidomimetic that is specific for the $\alpha_v\beta_3$-integrin, a cell-cell adhesion protein that is highly expressed in the peritumoral neovasculature. The amounts of paclitaxel contained in each emulsion were determined using the HPLC methods described previously. A first emulsion (KLN-0092-030) contained paclitaxel at 2.69 mg/ml, and a second emulsion (KLN-0092-029) contained paclitaxel at 1.82 mg/ml.

For a positive control, paclitaxel was obtained in a dry powder form from Phyton Biotech, LLC (Fort Worth, Tex.). A paclitaxel stock solution (30 mg/mL) in 50% ethanol: 50% Cremophor EL was prepared and stored protected from light at room temperature during the dosing period. On each day of dosing, an aliquot of the paclitaxel stock was diluted with 5% dextrose in water (D5W) to yield a 3.0 mg/mL paclitaxel dosing solution in a vehicle consisting of 5% ethanol: 5% Cremophor EL: 90% D5W in a 10 mL/kg dose volume.

Study Design: Six groups of ten NCr nu/nu mice were dosed according to the protocol outlined below. Doses were adjusted accordingly for body weights and were given by slow i.v. push. When doses were above 10 mL/kg they were split into two parts dosed 30 minutes apart.

Group 1 received no treatment and served as the benchmark group for tumor engraftment and progression as well as a negative control. See, Curve 210 FIG. 2).

Group 2 received KLN-0092-029 administered intravenously (i.v.), at 20 mg/kg, on Days 1 and 3, then 30 mg/kg on Days 5, 7 and 9, followed by 40 mg/kg on Day 15. These doses were given at 10.99, 16.48 and 21.98 mL/kg respectively. See, Curve 220, FIG. 2)

Group 3 received KLN-0092-029 i.v., at 40 mg/kg, on Days 1 and 3, followed by 30 mg/kg on Days 5, 7 and 9. These doses were given at 21.98 and 16.48 mL/kg respectively. See, Curve 230, FIG. 2).

Group 4 received KLN-0092-030 i.v., at 20 mg/kg on Days 1 and 3, then 30 mg/kg on Days 5, 7 and 9, followed by 40 mg/kg on Day 15. These doses were given at 7.43, 11.15 and 14.87 mL/kg respectively. See, Curve 240, FIG. 2).

Group 5 received KLN-0092-030 i.v., at 40 mg/kg, on Days 1 and 3, followed by 30 mg/kg on Days 5, 7 and 9. These doses were given at 14.87 and 11.15 mL/kg respectively. See, Curve 250, FIG. 2).

Group 6 received paclitaxel, i.v., at 30 mg/kg, every other day for a total of five doses. See, Curve 260, FIG. 2).

Toxicity: Animals were weighed daily for the first five days of the study and twice weekly thereafter. The mice were observed frequently for overt signs of any adverse, treatment-related (TR) side effects, and clinical signs of toxicity were recorded when observed. Individual body weight (BW)

loss was monitored as per protocol and any animal that exceeded the limits for acceptable BW loss was euthanized. Group mean body weight loss also was monitored as per protocol. Acceptable toxicity was defined as a group mean BW loss of less than 20% during the study and not more than 10% mortality due to TR deaths. Any dosing regimen resulting in greater toxicity was considered above the maximum tolerated dose (MTD). A death was classified as TR if attributable to treatment side effects as evidenced by clinical signs and/or necropsy, or if due to unknown causes during the dosing period or within fourteen days of the last dose. A death was classified as non-treatment-related (NTR) if there was no evidence that death was related to treatment side effects.

FIG. 2 shows the percent change in mean body weight for each group, based on the mean body weight for each group on the first day of dosing. No group reached the 20% reduction of body weight threshold for toxicity. There were no overt signs and symptoms of toxicity, and there were no treatment-related deaths on non-treatment-related deaths in any of the groups.

ticle arms showed a reduction in tumor size substantially similar to the positive control, and statistically very different ($p<0.001$) from the untreated arm. There were no treatment-related or non-treatment-related deaths in any of the nanoparticle emulsion arms.

Example 4: Demonstration of Targeting Effect

To demonstrate the benefit of targeting the nanoparticle emulsion, a study on A549 lung cancer mouse xenograft cancer models was carried out in which both targeted and untargeted nanoparticle emulsions were compared to positive (conventionally formulated paclitaxel) and negative (untreated) controls.

The study methods, design, and toxicity criteria were similar to what is presented in example 3, with the following exceptions: an A549 lung cancer xenograft model was used, and targeting was achieved by inclusion of peptidomimetic, TL-29, that is specific for the $\alpha_v\beta_3$-integrin, a cell-cell adhesion protein that is highly expressed in the peritumoral neovasculature. TL-29 is not known to be pharmacologically active against any cancers.

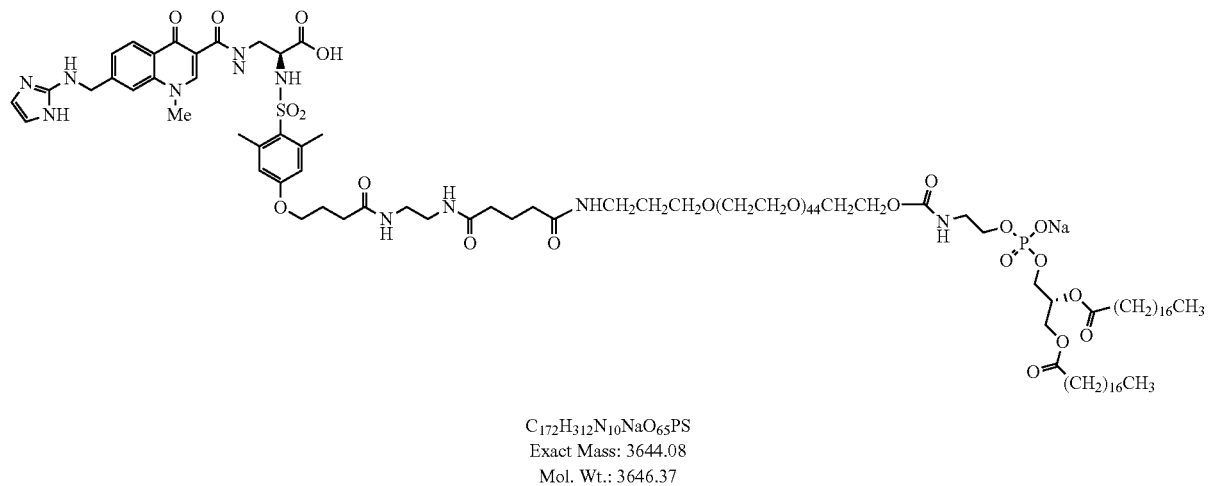

Note that the positive control was paclitaxel in a standard Cremophor EL formulation. The toxicity of Cremophor EL is sporadic and not always evident in animal models. The positive control was dosed within a well-established maximum tolerated dose, which was chosen so that minimal side effects and toxicities occur. Further, the dosing of the nanoparticle emulsion was very conservative, at about half the previously determined maximum tolerated dose in healthy normal mice. This was done to insure that most of the weakened tumored mice survived the study without unexpected toxicity or mortality. Because of this, there is no expectation of demonstrating superior toxicity profiles for either of the two nanoparticle emulsions over the conventionally formulated paclitaxel.

Figure 3:
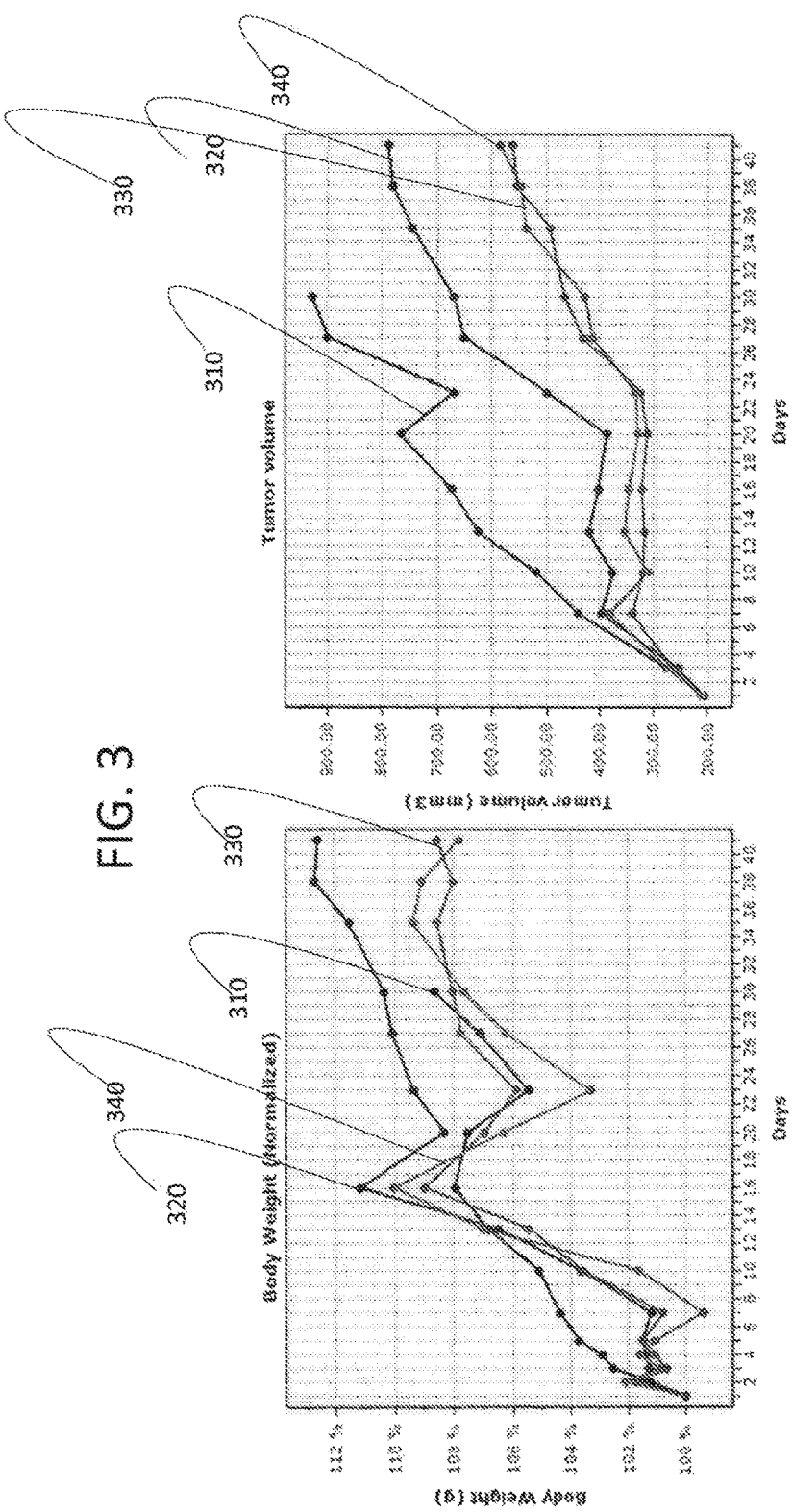
FIG. 3 graphically recites body weight changes, and tumor volume changes, over time for each treatment group identified.

Efficacy: Using the caliper method of measuring tumor size, as described above, the mean tumor size of each treatment group was followed for 60 days. The mean tumor size for each of these groups is shown in FIG. 3. In all cases, the $\alpha_v\beta_3$-integrin-targeted paclitaxel-containing nanopar- Formulation for the targeted emulsion was achieved as follows:

1.13 g tartaric acid (J. T. Baker) was dissolved in approximately 950 mL sterile water for injection (Baxter) in a 1 L beaker using magnetic stirring. Next 22.00 g glycerin (Mallinckrodt) was added with stirring. The pH of the buffer solution was then adjusted to final pH of 4.50 using 1 N sodium hydroxide (VWR). Finally the solution was brought to a final volume of 1 L using sterile water for injection (Baxter).

Next, 213.6 mg of paclitaxel (PTX; Tecoland) was dissolved in 6 mL of triacetin (Sigma) by rotating a 25 mL single neck round bottom flask containing the paclitaxel and triacetin in a heated (41° C.) sonicating bath for 30 min using a Büchi R-200 Rotavapor.

2.14 g of purified egg phosphatidylcholine (Lipoid) and 10.6 mg of $\alpha_v\beta_3$-TL 29 targeting ligand, a petidomimetic (Kereos; KLN-0062-095B1) were homogenized in 84 mL of pH 4.50 7.5 mM tartrate buffer with 22 mg/mL glycerin for 30 seconds in a 250 mL disposable beaker using an Ultra-Turrax T25 rotor stator homogenizer. Next, 17 mL of safflower oil (Sigma) was added to the contents of the beaker, followed by the addition of the PTX/triacetin solution, and the combined components homogenized for an additional 2 minutes. The resulting crude emulsion was then processed on a M-110-EH Microfluidizer (Microfluidics) at approximately 20,000 psi for 13 minutes at a temperature of 5° C. and flow rate of 410 mL/min. A post-processing particle size measurement showed a distribution with a median of 0.1525 μm and a mean of 0.1693 μm with a small population (0.7%) ranging from approximately 0.15 μm to approximately 0.3 μm. The fine emulsion was then extruded through twenty 0.45 μm syringe filters (Whatman Puradisc 25 PP syringe filters with 0.45 μm polypropylene media) using a 60 mL disposable syringe (BD). The filtered emulsion was then vialed in Wheaton 5 mL serum sample vials with a 5 mL fill and stoppered and sealed with rubber stoppers and Flip-Off seals (West Pharmaceutical). Post formulation HPLC analysis showed the paclitaxel concentration at 1.85 mg/mL.

A Non-Targeted Formulation was made as Follows:

1.13 g tartaric acid (J. T. Baker) was dissolved in approximately 950 mL sterile water for injection (Baxter) in a 1 L beaker using magnetic stirring. Next 22.00 g glycerin (Mallinckrodt) was added with stirring. The pH of the buffer solution was then adjusted to final pH of 4.50 using 1 N sodium hydroxide (VWR). Finally the solution was brought to a final volume of 1 L using sterile water for injection (Baxter).

240.0 mg of paclitaxel (PTX; Tecoland) was dissolved in 7 mL of triacetin (Sigma) by rotating a 25 mL single neck round bottom flask containing the paclitaxel and triacetin in a heated (41° C.) sonicating bath for 1 hour and 15 min using a Büchi R-200 Rotavapor.

240 g of purified egg phosphatidylcholine (Lipoid) was homogenized in 94 mL of pH 4.50 7.5 mM tartrate buffer with 22 mg/mL glycerin for 30 seconds in a 250 mL disposable beaker using an Ultra-Turrax T25 rotor stator homogenizer. Next 19 mL of safflower oil (Sigma) was added to the contents of the beaker, followed by the addition of the PTX/triacetin solution and the combined components homogenized for an additional 2 minutes. The resulting crude emulsion was then processed on a M-110-EH Microfluidizer (Microfluidics) at approximately 20,000 psi for 14 minutes 30 seconds at a temperature of 5° C. and a flow rate of 410 mL/min. A post-processing particle size measurement showed a distribution with a median of 0.1462 μm and a mean of 0.1634 μm with a small population (0.7%) ranging from approximately 1 μm to approximately 2 μm. The fine emulsion was then extruded through twenty 0.45 μm syringe filters (Whatman Puradisc 25 PP syringe filters with 0.45 μm polypropylene media) using a 60 mL disposable syringe (BD). The filtered emulsion was then vialed in Wheaton 5 mL serum sample vials with a 5 mL fill and stoppered and sealed with rubber stoppers and Flip-Off seals (West Pharmaceutical). Post formulation HPLC analysis showed the paclitaxel concentration at 1.85 mg/mL.

The study design is shown in the following table, and the tumor size and body weights are shown in table 2. See also, Curves 310, 320, 330, and 340, FIG. 3.

TABLE 2

| | | Treatment Regimen | | | |
|---|---|---|---|---|---|
| Group | n | Agent | mg/kg | Route | Schedule |
| 1 | 10 | No Treatment | — | — | — |
| 2 | 10 | non-targeted PTX | 40 | iv | qd x 5 |
| 3 | 10 | aVb3-targeted PTX | 40 | iv | qd x 5 |
| 4 | 10 | paclitaxel | 15 | iv | qd x 5 |

There was no excessive toxicity in this study. No group had a mean weight loss greater than 20%. The mean tumor responses and body weights are shown in FIG. 5. There is a statistically significant difference between the non-targeted and the targeted arms, with the targeted arm showing efficacy that is statistically insignificantly different than the positive control. The mean tumor volume at the study endpoint for the untargeted nanoparticle formulation was 726 mm$^3$ and the mean tumor volume for the targeted nanoparticle formulation was 446 mm$^3$. These statistically significant differences demonstrate the added value of targeting the nanoparticle emulsion.

Example 5. Demonstration of a Cisplatin-Containing Emulsion

In order to demonstrate the ability to incorporate a water-soluble small molecule therapeutic into the nanoparticle emulsion, a formulation containing cisplatin was achieved as follows:

1.03 g sodium phosphate monobasic monohydrate acid (Mallinckrodt) was dissolved in approximately 950 mL sterile water for injection (OmniPur) in a 1 L beaker using magnetic stirring. Next 22.00 g glycerin (Mallinckrodt) was added with stirring. The pH of the buffer solution was then adjusted to final pH of 6.50 using 1 N sodium hydroxide (VWR). Finally the solution was brought to a final volume of 1 L using sterile water for injection (OmniPur).

Next, 50.0 mg of cisplatin (CDDP; Tecoland) was suspended in 7 mL of safflower oil (Spectrum) by vortexing a 4 dram vial containing the cisplatin and safflower oil for 30 seconds then immersing it in a heated (41° C.) sonicating bath for 15 min. The vial and its contents were then vortexed again for 30 seconds immediately prior to use.

0.70 g of purified egg phosphatidylcholine (Lipoid), 150 mg of dipalmitoyl-sn-glycero-3-phosphoglycerol (DPPG; Lipoid) and 150 mg of 1,2-distearoyl-sn-glycero-3-phosphoethanolamine-N-[methoxy(polyethylene glycol)-550] (DSPE-PEG550; Avanti) were homogenized in 41 mL of pH 6.50 7.5 mM phosphate buffer with 22 mg/mL glycerin for 30 seconds in a 100 mL disposable beaker using an Ultra-Turrax T25 rotor stator homogenizer. Next, 7 mL of safflower oil with 50.0 mg of cisplatin suspended in it was added to the contents of the beaker, followed by the addition of 2 mL of triacetin (Spectrum) and the combined components homogenized for an additional 2 minutes 30 seconds. The resulting crude emulsion was then processed on a M-110-Y Microfluidizer (Microfluidics) at approximately 16,000 psi for 5 minutes with ice water being used to cool the heat exchanger of the Microfluidizer. The fine emulsion was then sterile filtered through a single 32 mm 0.20 μm syringe filter (Pall Acrodisc PF syringe filter with 0.2 μm Supor polyethersulfone media) using a 60 mL disposable syringe (BD). The sterile-filtered emulsion was then vialed in Wheaton 5 mL serum sample vials with a 5 mL fill and stoppered and sealed with rubber stoppers and Flip-Off seals (West Pharmaceutical). Post formulation HPLC analysis showed the cisplatin concentration at 0.47 mg/mL.

Negative control vehicle was formulated as follows: 1.03 g sodium phosphate monobasic monohydrate acid (Mallinckrodt) was dissolved in approximately 950 mL sterile water for injection (OmniPur) in a 1 L beaker using magnetic stirring. Next 22.00 g glycerin (Mallinckrodt) was added with stirring. The pH of the buffer solution was then adjusted to final pH of 6.50 using 1 N sodium hydroxide (VWR). Finally the solution was brought to a final volume of 1 L using sterile water for injection (OmniPur).

0.70 g of purified egg phosphatidylcholine (Lipoid), 150 mg of dipalmitoyl-sn-glycero-3-phosphoglycerol (DPPG; Lipoid) and 150 mg of 1,2-distearoyl-sn-glycero-3-phosphoethanolamine-N-[methoxy(polyethylene glycol)-550] (DSPE-PEG550; Avanti) were homogenized in 41 mL of pH 6.50 7.5 mM phosphate buffer with 22 mg/mL glycerin for 30 seconds in a 100 mL disposable beaker using an Ultra-Turrax T25 rotor stator homogenizer. Next 7 mL of safflower oil (Spectrum) was added to the contents of the beaker, followed by the addition of 2 mL of triacetin (Spectrum) and the combined components homogenized for an additional 2 minutes 30 seconds. The resulting crude emulsion was then processed on a M-110-Y Microfluidizer (Microfluidics) at approximately 16,000 psi for 5 minutes with ice water being used to cool the heat exchanger of the Microfluidizer. The fine emulsion was then sterile filtered through a single 32 mm 0.20 μm syringe filter (Pall Acrodisc PF syringe filter with 0.2 μm Supor polyethersulfone media) using a 60 mL disposable syringe (BD). The sterile-filtered emulsion was then vialed in Wheaton 5 mL serum sample vials with a 5 mL fill and stoppered and sealed with rubber stoppers and Flip-Off seals (West Pharmaceutical).

Figure 4:
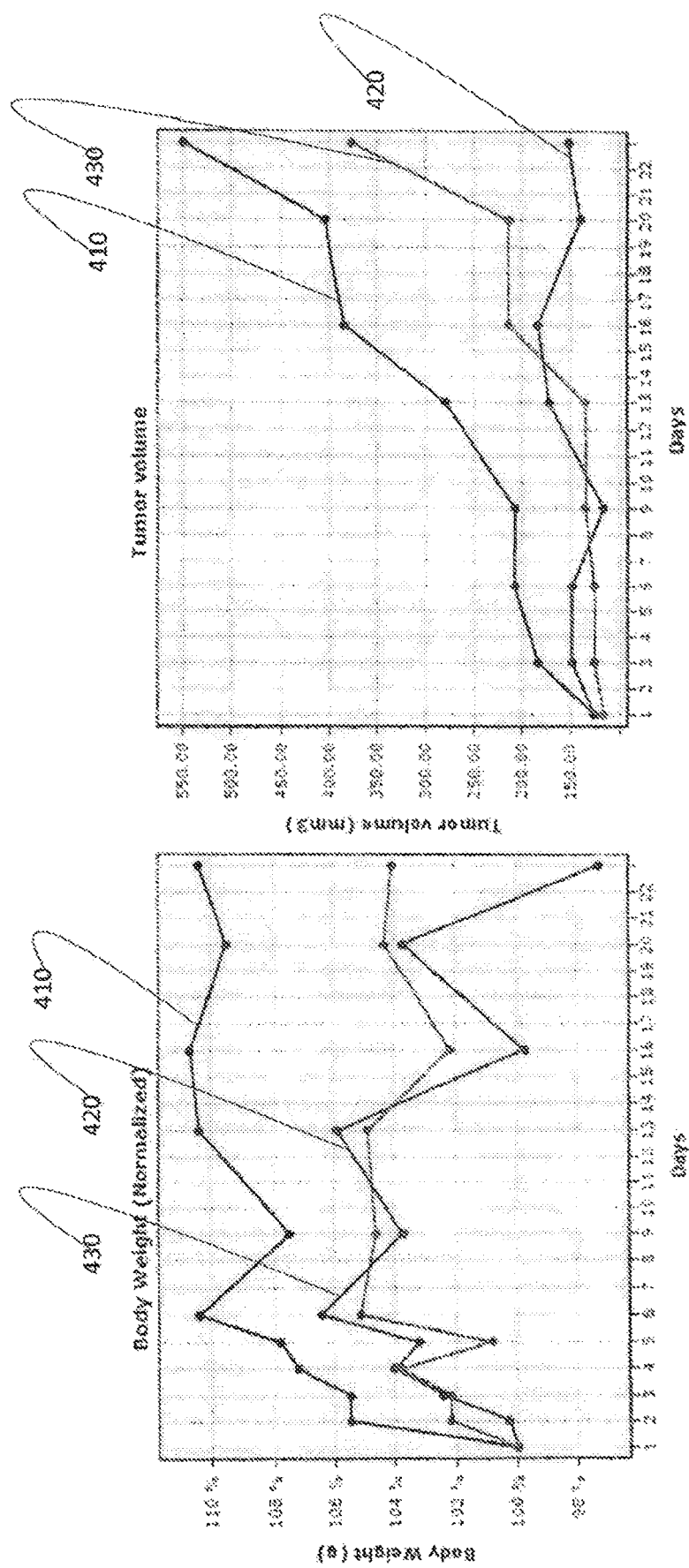
FIG. 4 graphically recites body weight changes, and tumor volume changes, over time for each treatment group identified. The cisplatin nanoparticle formulation (labeled HJ9 in FIG. 4) effected a significant reduction in tumor growth, as did the positive control of free cisplatin.

Next, demonstration of efficacy of this formulation was carried out on OVCAR3 human ovarian carcinoma xenograft models using female CB.17 SCID mice, the results of which are shown in Curves 410, 420, and 430, FIG. 4. In this three-arm study, a vehicle control was included, which consisted of the nanoparticle emulsion with no cisplatin. A positive control arm included a conventional formulation of free cisplatin dosed at 4 mg/kg. The test arm included the nanoparticle emulsion at a dose of 4 mg/kg.

60 female CB.17 SCID mice, aged 8 to 12 weeks, were implanted with ~1 mm$^3$ OVCAR3 tumor fragments in the flank. When the tumors had grown to approximately 100-150 mm$^3$, pairs were matched by tumor size and treatment began. Dosing was carried out weekly on all three arms, for a total of four doses. Body weight and tumor size for each of the mice was taken every other day. Mean tumor size and normalized mean body weights are shown in FIG. 5. No excess toxicity was noted, as evidenced by body weight and observed behavior of the mice. The cisplatin nanoparticle formulation (labeled HJ9 in FIG. 6) effected a significant reduction in tumor growth, as did the positive control of free cisplatin. The negative control (labeled 'vehicle' in FIG. 6) served as a reference for tumor growth in the absence of cisplatin.

Example 6. Treatment of Cancer in Humans

In accordance with the invention described herein, a prophetic example of its utility in the treatment of cancer in humans is provided.

A nanoparticle emulsion is formulated substantially as described in example 1. Initial human safety trials are conducted with the nanoparticle emulsion according to standard clinical protocols to determine maximum tolerated dose (MTD) in humans. Efficacy studies are then conducted in humans to determine optimal dosing schedules for various types of cancer, where optimal dosing is determined by a combination of toxicity, tolerability, and tumor response. Dosing schedules may include intensive daily dosing, metronomic dosing (lower doses administered daily over extended periods of time), or less frequent but higher doses, as determined by clinical responses observed in the efficacy studies.

Patients with cancer types and sub-types that respond to the described nanoparticle formulation are then given appropriate treatment and monitored for response. Patients may receive multiple treatments consistent with acceptable toxicity and continued tumor response.

Example 7: Alternative Formulations

In a first alternative example, formulation of a nanoparticle emulsion was formulated as described in example 1, except the ratio of safflower oil to triacetin was 1:1 instead of 7:2 (safflower oil in excess). The crude emulsion was formulated using the microfluidization process described above, and the fine emulsion was characterized with respect to particle size. Immediately after formulation it was found that the mean particle diameter was over 200 nanometers, with a very asymmetric distribution that included a significant population of particles greater than 1 micrometer in diameter. Pools of free lipids were observed shortly after formulation, and within a day most of the nanoparticles had disintegrated, as demonstrated by static light scattering measurements, and there was visible phase separation in the bulk formulation.

In a second alternative example, formulation of a nanoparticle emulsion was attempted as described in example 1, except that pure linoleic acid was used instead of safflower oil. Linoleic acid is the predominant lipid in safflower oil, so it was anticipated that it might be a useful substitute for safflower oil. The initial steps were carried out as described in example 1, but during formulation of the crude emulsion using high shear mixing there was significant foaming that prevented further processing to produce the fine emulsion. The formulation process was aborted at this point. Subsequent attempts to produce a nanoparticle emulsion with pure linoleic acid have proven unsuccessful.

In a third alternative example, formulation of a nanoparticle emulsion was attempted as described in example 1, except that pure oleic acid was substituted for the safflower oil. The initial steps were carried out as described in example 1, but during formulation of the crude emulsion using high shear mixing there was significant foaming that prevented further processing to produce the fine emulsion. The formulation process was aborted at this point. Subsequent attempts to produce a nanoparticle emulsion with pure oleic acid have proven unsuccessful.

In a fourth alternative example, formulation of a nanoparticle emulsion was attempted as described in example 1, except that no safflower oil was used, just triacetin as the lipid component. The initial steps were carried out as described in example 1, but it was not possible to produce even a crude emulsion as the triacetin came out of solution too quickly and formed distinct phase separation. Subsequent attempts to produce a nanoparticle emulsion with pure triacetin acid have proven unsuccessful.

In a fifth alternative example, formulation of a nanoparticle emulsion was attempted as described in example 1, except that no triacetin was used, just safflower oil as the lipid component. The initial steps were carried out as described in example 1, but it was not possible dissolve enough paclitaxel in the safflower oil to be clinically useful. The maximum solubility was approximately 1000× less than in triacetin. Although it was possible to produce a stable fine nanoparticle emulsion with just safflower oil as the lipid component, suggesting possible formulations for APIs that are soluble in pure safflower oil, the amount of paclitaxel incorporated into the fine emulsion was far below what is required for therapeutic efficacy.

In a sixth alternative example, formulation of a nanoparticle emulsion was attempted as described in example 1, except that the surfactant commixture consisted entirely of DPPC and the ratio of safflower oil to triacetin was 8:3 instead of 7:2. A crude emulsion was successfully formulated as described in example 1. However, the microfluidization method of formulating the fine emulsion resulted in a preponderance of particles that were larger than 1 micrometer, and which were unstable.

In a seventh alternative example, formulation of a nanoparticle emulsion was attempted as described in example 1, except that the surfactant commixture consisted entirely of DPPC and the ratio of safflower oil to triacetin was kept at 7:2. A crude emulsion was successfully formulated as described in example 1. However, the microfluidization method of formulating the fine emulsion resulted in a preponderance of particles that were larger than 200 nanometers, and which was unable to be sterile-filtered.

While the preferred embodiments of the present invention have been illustrated in detail, it should be apparent that modifications and adaptations to those embodiments may occur to one skilled in the art without departing from the scope of Applicants' disclosure.

We claim:

1. A nanoparticle pharmaceutical delivery system, comprising:

12-28% (v/v) type 1 safflower oil;

1.5-12% (v/v) triacetin;

1.5-5.0% (w/v) surfactant commixture of dipalmitoylphosphatidylcholine and dipalmitoylphosphatidylglycerol; and 0.1 to 0.6% (w/v) of one or more active pharmaceutical ingredients (APIs).

2. The nanoparticle pharmaceutical delivery system of claim 1, wherein said one or more APIs comprises a taxane, further comprising:

a platinum derivate;

1-4% (w/v) glycerin; and buffered water at pH below 8.0.

3. The nanoparticle pharmaceutical delivery system of claim 2, wherein the taxane is docetaxel or paclitaxel, and wherein the platinum derivative is carboplatin or cisplatin.

4. The nanoparticle pharmaceutical delivery system of claim 1, wherein said one or more APIs is selected from the group consisting of taxanes and platinum derivatives.

5. The nanoparticle pharmaceutical delivery system of claim 1, wherein said one or more APIs is selected from the group consisting of docetaxel, paclitaxel, carboplatin, and cisplatin.

* * * * *